Figure 1:
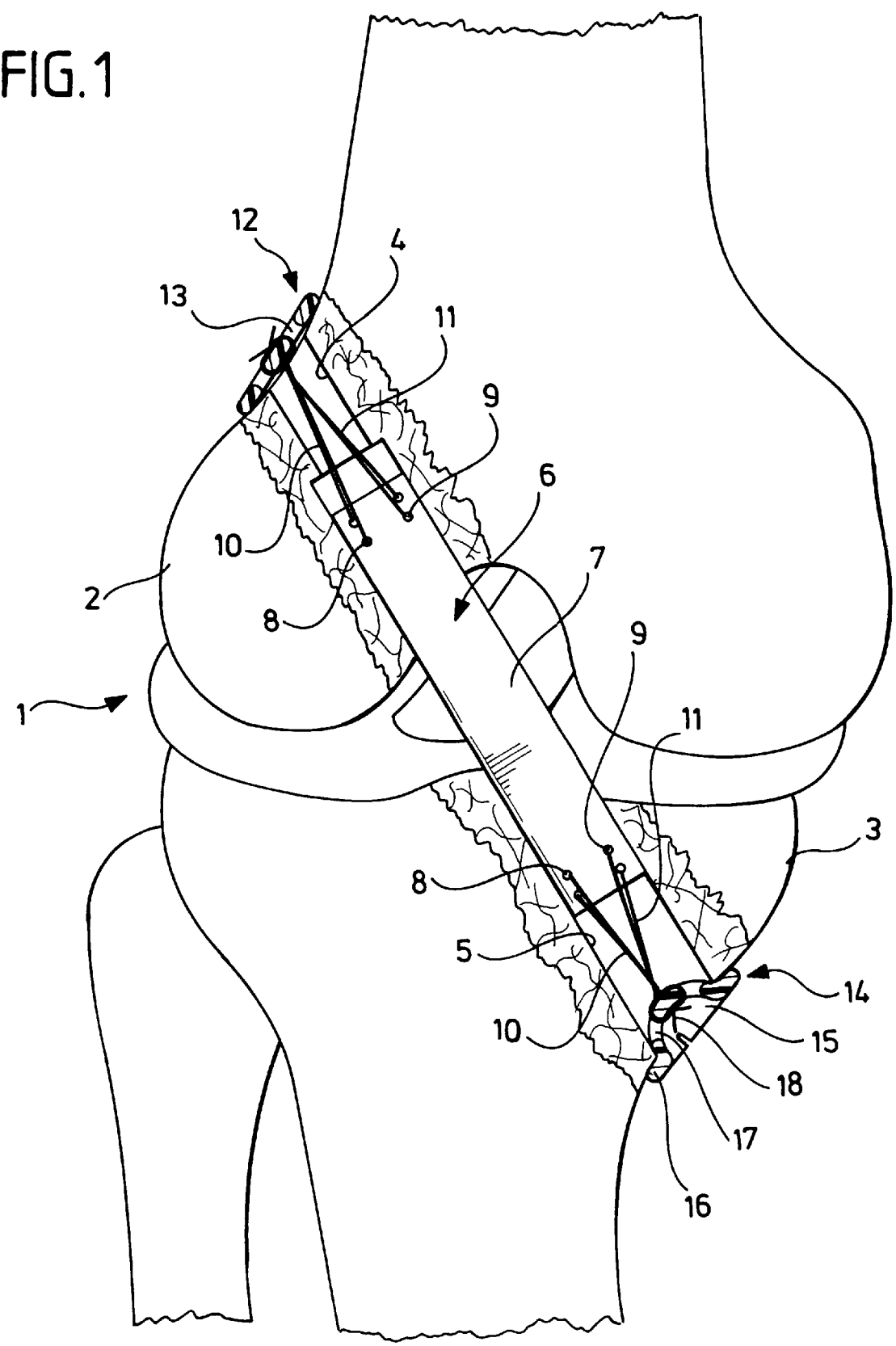

United States Patent
Giordano et al.

[11] Patent Number: 6,042,609
[45] Date of Patent: Mar. 28, 2000

[54] IMPLANT FOR FIXING A PLASTIC REPLACEMENT FOR A TENDON

[75] Inventors: Nicola Giordano, Villingen-Schwenningen; Theodor Lutze, Balgheim; Rudolf Henche, Rheinfelden, all of Germany

[73] Assignee: Aesculap AG & Co. KG, Tuttlingen, Germany

[21] Appl. No.: 08/972,957

[22] Filed: Nov. 19, 1997

[30] Foreign Application Priority Data

Nov. 28, 1996 [DE] Germany .............. 196 49 450

[51] Int. Cl.[7] .......................................... A61F 2/08
[52] U.S. Cl. .................................. 623/13; 623/16
[58] Field of Search .................. 623/13, 16, 19

[56] References Cited

U.S. PATENT DOCUMENTS

| | | | |
|---|---|---|---|
| 3,808,606 | 5/1974 | Tronzo . | |
| 3,896,500 | 7/1975 | Rambert et al. ............. | 623/13 |
| 4,676,798 | 6/1987 | Noiles ....................... | 623/19 |
| 4,793,335 | 12/1988 | Frey et al. ................. | 623/13 |
| 5,047,058 | 9/1991 | Roberts et al. ............. | 623/16 |
| 5,314,480 | 5/1994 | Elloy ........................ | 623/16 |
| 5,425,766 | 6/1995 | Bowald ...................... | 623/13 |
| 5,531,792 | 7/1996 | Huene ....................... | 623/13 |
| 5,643,266 | 7/1997 | Li ............................ | 623/13 |
| 5,645,589 | 7/1997 | Li ............................ | 623/13 |
| 5,690,649 | 11/1997 | Li ............................ | 623/13 |

FOREIGN PATENT DOCUMENTS

| | | |
|---|---|---|
| 2 703 239 | 10/1994 | France . |
| 296 07 352 U | 9/1996 | Germany . |

*Primary Examiner*—Paul J. Hirsch
*Attorney, Agent, or Firm*—Barry R. Lipsitz; Ralph F. Hoppin

[57] ABSTRACT

In an implant for fixing a plastic replacement for a tendon at a channel accommodating the plastic tendon replacement in the area of the tibia near the knee in the form of a disc having through-openings for threads joined to the plastic tendon replacement and being of such dimensions that it completely covers the opening of the channel exiting from the tibia, in order to prevent rotation of the implant with respect to the tibia head, the disc comprises on its underside facing the tibia projections for preventing the disc from rotating relative to the tibia.

8 Claims, 3 Drawing Sheets

IMPLANT FOR FIXING A PLASTIC REPLACEMENT FOR A TENDON

The present disclosure relates to the subject matter disclosed in application No. 196 49 450.8 of Nov. 28, 1996, the entire specification of which is incorporated herein by reference.

The invention relates to an implant for fixing a plastic replacement for a tendon at a channel accommodating the plastic tendon replacement in the area of the tibia near the knee in the form of a disc having through-openings for threads joined to the plastic tendon replacement and being of such dimensions that it completely covers the opening of the channel exiting from the tibia.

Such an implant is known from German Utility Model 90 02 844 and from German Utility Model 29 607 352.

When inserting a plastic replacement for a tendon it must be tensioned in a certain way. It is very difficult to obtain exactly the desired tension by knotting threads which join the plastic tendon replacement to the implant. It is, therefore, desirable for this tension to be adjusted to a slight extent after the knotting of the threads. This is achievable by the disc-shaped implant being turned about the longitudinal axis of the channel exiting from the tibia. Pairs of threads lying next to one another and joining the plastic tendon replacement to the implant can thereby be twisted together, and this twisting results in an effective shortening of these threads, i.e., the tension of the plastic tendon replacement can thereby be increased.

The object of the invention is to so design a generic implant that such thread shortening and increasing of the tension of the plastic tendon replacement can be permanently maintained.

This object is accomplished in accordance with the invention with an implant of the kin d described at the outset in that the disc comprises on its underside facing the tibia projections for preventing the disc from rotating relative to the tibia.

These projections interact with the material of the tibia and prevent the disc-shaped implant from rotating about the longitudinal axis of the channel. The twisting of the threads holding the plastic tendon replacement can thereby be maintained, and, in this way, also the increased tension of the plastic tendon replacement produced by the twisting.

The projections fixing the disc relative to the tibia can vary widely in design. For example, these projections can be downwardly projecting tips.

These tips can be permanently connected to the disc. In a preferred embodiment, the tips can also be formed by pins which extend through apertures in the disc. The pins can then be in the form of, for example, a nail or a screw which is fixed in the bone material.

In this case, it is advantageous for the apertures to be closed, i.e., to be formed by openings penetrating the disc.

In another embodiment, the apertures are open towards the outer edge of the disc, thereby forming indentations in the disc which extend inwardly from the edge and through which a pin passes.

In a further preferred embodiment, the projections comprise downwardly protruding edges which grip into the material of the tibia and thereby prevent rotation of the disc.

The projections may be formed by downwardly bent flaps of the disc.

In this case, it is advantageous for the flaps to be separated off from the disc by at least one cut which does, however, leave the flaps joined in areas thereof to the disc. The projections are then produced by merely bending the flaps out of the plane of the disc, and this bending is carried out either during manufacture of the implant or only after insertion of the implant by the operator.

In a first embodiment, the cut extends inwardly at an incline form the outer edge. Such a configuration has the advantage that the flap tapers at its free end and forms a tip in the downwardly bent state.

In another embodiment, the cut can have a first section which extends radially inwardly from the outer edge and is adjoined by a section which extends essentially in the circumferential direction. Such a flap has at its free end an edge which extends in the radial direction and digs into the bone material when the flap is bent downwards.

It is expedient for two flaps to be arranged on diametrically opposed sides of the disc.

Figure 2:
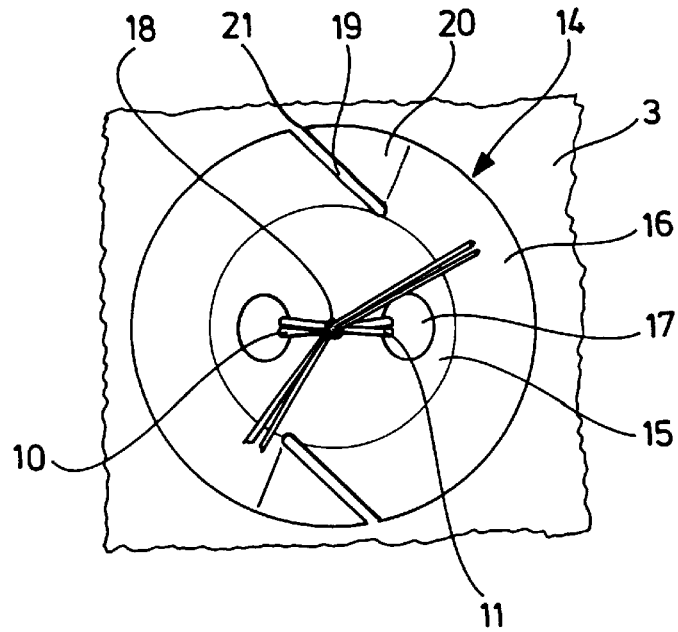
Figure 3:
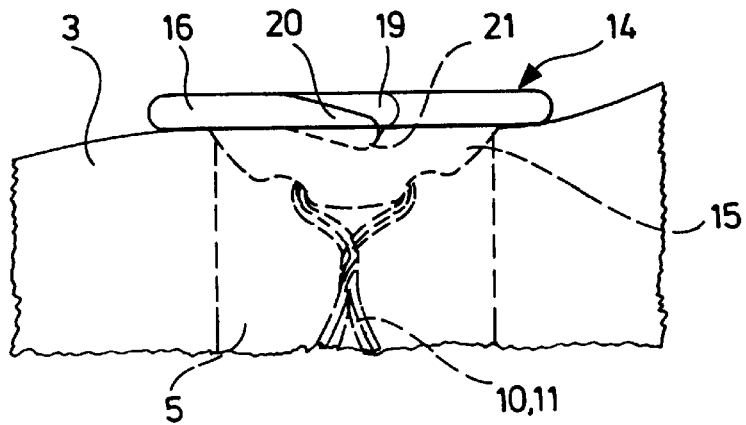
Figure 4:
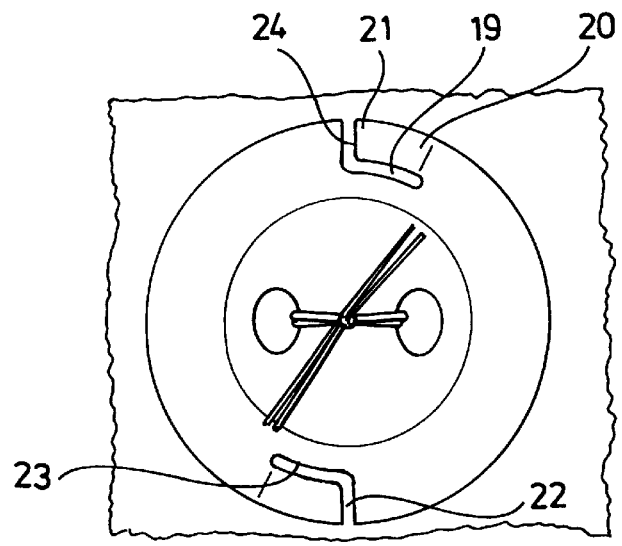
Figure 5:
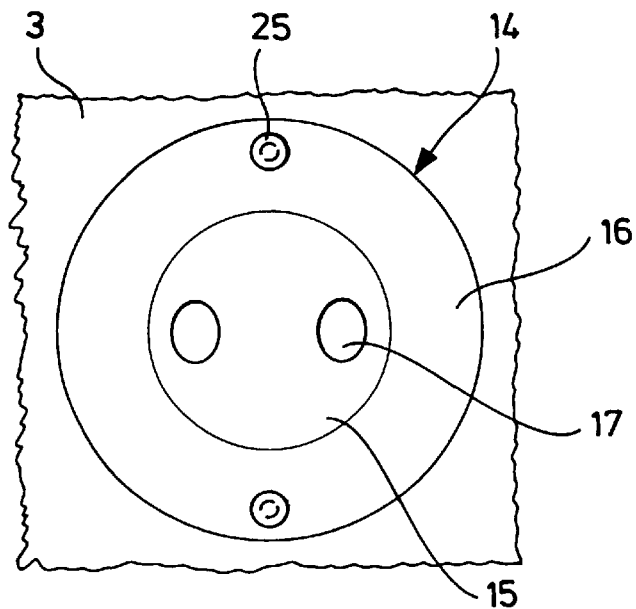
Figure 6:
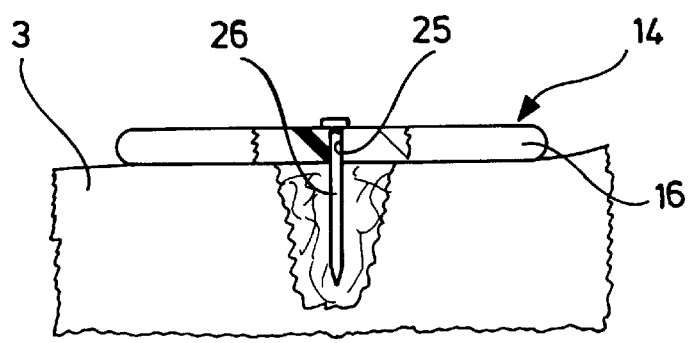

The following description of preferred embodiments of the invention serves in conjunction with the drawings to explain the invention in greater detail. The drawings show:

FIG. 1 a side view of a knee joint with a plastic replacement for a cruciate ligament in a representation broken open in the area of the bone channels;

FIG. 2 a plan view of a disc-shaped implant with flaps formed by oblique cuts;

FIG. 3 a side view of the implant of FIG. 2;

FIG. 4 a view similar to FIG. 2 of an implant with an L-shaped cut;

FIG. 5 a plan view of a further preferred embodiment of an implant with through-openings for retaining pins;

FIG. 6 a side view of the implant of FIG. 5; and

Figure 7:
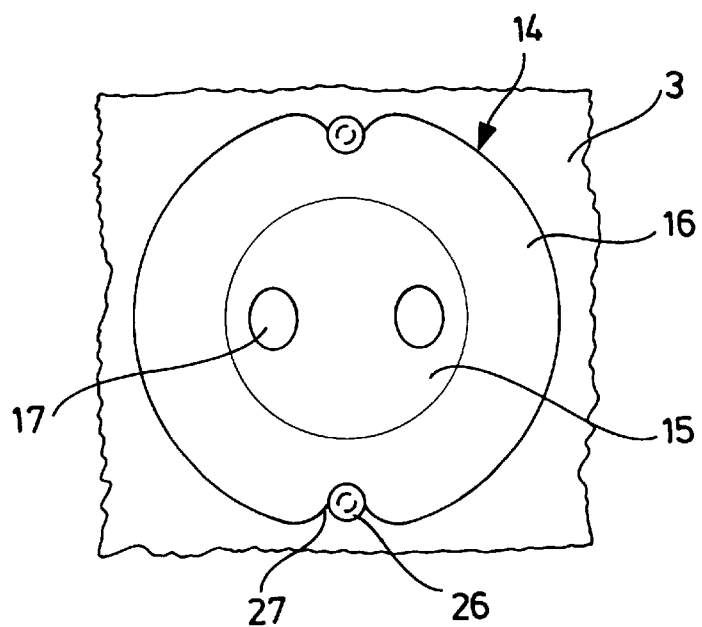

FIG. 7 a view similar to FIG. 5 with apertures open at the side for receiving retaining pins.

In order to replace a destroyed cruciate ligament in a knee joint 1, a longitudinal channel 4 is drilled in the femur head 2 and a longitudinal channel 5 in the tibia head 3. When the knee joint is stretched, these channels are essentially in alignment with each other and extend at an incline through the knee joint from the front side to the rear side thereof.

A plastic cruciate ligament replacement 6 is drawn into the longitudinal channels 4 and 5. The plastic cruciate ligament replacement 6 comprises a band-shaped piece 7 of a plastic replacement for a tendon, for example, part of the patellar tendon. Arranged at the ends of the plastic tendon replacement are threads 10, 11 drawn through openings 8, 9, for example, two threads 10 and 11 arranged next to each other at both ends, as shown in the illustration of FIG. 2.

To fix the piece 7 in the longitudinal channels 4, 5, the threads 10, 11 are guided out of the longitudinal channels 4, 5 and fixed at the outside thereof. Arranged at the exit of the longitudinal channel 4 is a button-shaped implant 12 with two through-openings 13 through which the threads 10, 11 are passed. They are knotted together on the side of the implant 12 facing away from the bone so the threads 10, 11 are held on the implant 12 resting on the femur head 2 (FIG. 1).

An implant 14 having a spherically bulging central area 15 and a flat edge strip 16 surrounding it in the shape of a ring so the implant 14 has a hat-shaped appearance is used on the opposite side in the area in which the longitudinal channel 5 exits from the tibia head 3. Two through-openings 17 through which the threads 10, 11 are drawn are provided in the central area 15.

The implant 14 is pushed into the exit opening of the longitudinal channel 5 such that the inwardly bulging central area 15 dips into the longitudinal channel 5 and thereby centers the hat-shaped implant 14 in the exit opening. The edge strip 16 positions itself on the outer surface of the tibia head 3 surrounding the exit opening of the longitudinal channel 5.

The two threads 10 and 11 passing through the through-openings 17 are tied together on the side facing away from the longitudinal channel 5, and the resulting knot 18 is accommodated in the hollow of the central area 15 facing away from the bone so the knot 18 does not protrude outwardly over the contour of the implant (FIG. 1).

The implant 14 is secured against rotation so as to prevent the inserted implant 14 from rotating about the longitudinal axis of the longitudinal channels 4, 5 when the implant 14 is pulled by the plastic cruciate ligament replacement 6 against the outer surface of the tibia head 3.

In a first embodiment (FIGS. 2 and 3), the protection against rotation is achieved by two oblique cuts 19 being made in the flat edge strip 16 from the outer edge and on diametrically opposed sides thereof. The two oblique cuts 19 divide essentially triangular flaps 20 off from the edge strip 16. These flaps 20 can be bent downwards, i.e., in the direction towards the tibia head 3, out of the plane of the edge strip 16, so the pointed free end 21 of the flaps 20 protrudes downwardly. An implant 14 of such design can be readily rotated in one direction of rotation after insertion, but upon rotation in the opposite direction the pointed free end 21 digs into the material of the tibia head 3 and prevents any rotation. Therefore, after insertion of the plastic cruciate ligament replacement 6, the operator can twist the threads 10, 11 around one another by rotating the implant 14 so their effective length decreases and the tension of the plastic cruciate ligament replacement 6 is increased. However, the implant 14 is no longer able to rotate back as the free ends 21 of the flaps 20 dig into the tibia head 3 in the described manner and prevent any further rotation in this direction.

In the embodiment of FIG. 4, which largely corresponds to that of FIG. 2, the cuts 19 are not of oblique configuration, but L-shaped. The cuts 19, therefore, have a first section 22 extending radially inwardly from the outer edge and an adjoining second section 23 extending essentially in the circumferential direction. Together, these divide off from the edge strip 16 an essentially rectangular flap 20 which ends at its free end 21 in the form of a radially extending edge 24. This flap 20 also forms a downwardly protruding projection when the flap is bent downwards out of the plane of the edge strip 16, and the edge 24 acts in the described manner to prevent rotation.

In the embodiment of FIG. 5, which again shows an implant of essentially identical design, the protection against rotation is not produced by cuts in the edge strip 16 but by openings 25 in the edge strip 16 with pins 26 which are inserted through these openings 25 so as to penetrate the tibia head 3 and thereby prevent any rotation of the implant 14. The pins 26 may, for example, be bone nails or bone screws.

Whereas in the embodiment of FIGS. 5 and 6, the openings 25 are closed through-openings, the implant of FIG. 7 has on opposite sides thereof indentations 27 extending inwards from the outer edge. Pins 26 are inserted in this area into the tibia head 3 and engage the indentations 27, thereby preventing any rotation of the implant. The pins 26 also act in this way as projections extending downwards from the implant, even though they are not necessarily fixedly connected to the implant in the embodiments of FIGS. 5 to 7.

What is claimed is:

1. An implant for fixing a plastic tendon replacement within a channel in an area of the tibia near the knee, comprising:

a disc with through-openings for receiving threads joined to the plastic tendon replacement;

said disc being adapted to completely cover an end opening in said channel; and at least one projection formed by a bent flap on an underside of said disc facing said tibia, said flap extending away from said disc toward said tibia and being formed by at least one cut in the disc that leaves the flap joined to the disc;

wherein the at least one projection prevents said disc from rotating relative to said tibia.

2. An implant as defined in claim 1 wherein said flap has edges that protrude toward said tibia.

3. An implant as defined in claim 1 wherein said cut extends inwardly at an incline from an outer edge of said disc.

4. An implant as defined in claim 1 wherein said cut has a first section extending into said disc from said outer edge and an adjoining second section extending from said first section in an essentially circumferential direction with respect to said disc.

5. An implant as defined in claim 4 wherein two flaps are provided on diametrically opposed sides of said disc.

6. An implant as defined in claim 3 wherein two flaps are provided on diametrically opposed sides of said disc.

7. An implant as defined in claim 2 wherein two flaps are provided on diametrically opposed sides of said disc.

8. An implant as defined in claim 1 wherein two flaps are provided on diametrically opposed sides of said disc.

* * * * *